(12) United States Patent
DeMayo

(10) Patent No.: US 6,685,655 B2
(45) Date of Patent: Feb. 3, 2004

(54) SURGICAL LEG LENGTH CONTROL

(75) Inventor: Edward DeMayo, Greenbrae, CA (US)

(73) Assignee: Innovative Medical Products, Plainville, CT (US)

( * ) Notice: Subject to any disclaimer, the term of this patent is extended or adjusted under 35 U.S.C. 154(b) by 280 days.

(21) Appl. No.: 09/978,506

(22) Filed: Oct. 18, 2001

(65) Prior Publication Data
US 2003/0078520 A1 Apr. 24, 2003

(51) Int. Cl.[7] ............................ A61B 17/56; A61B 17/64
(52) U.S. Cl. .................................. 600/587; 606/102
(58) Field of Search ............................ 606/53, 86, 102; 33/511; 600/587

(56) References Cited

U.S. PATENT DOCUMENTS 6,027,507 A * 2/2000 Anderson et al. ............ 606/102
6,477,400 B1 * 11/2002 Barrick ........................ 600/427

* cited by examiner

Primary Examiner—Max F. Hindenburg
Assistant Examiner—David J. McCrosky

(57) ABSTRACT

A hand-held leg length discrepancy device in the form of an extended pin separated a fixed distance from a laser diode determines the length of a patient's leg after hip replacement surgery. A self-tapping first indication screw is partially inserted within the patient's pelvis prior to surgery, the extended pin is positioned on the screw and the laser beam is directed on the patient's leg. The location of the laser beam is recorded by means of an indelible ink mark or a drill hole. After surgery, the extended pin is positioned on the screw on the hip and the laser beam is again directed on the second mark or drill hole on the leg to determine any change in distance there between.

5 Claims, 3 Drawing Sheets

SURGICAL LEG LENGTH CONTROL

BACKGROUND OF THE INVENTION

It is difficult during joint replacement within the human body to maintain the exact overall leg dimension after surgery. This is especially true when large joints such as hips, are repaired and or completely replaced. A good description of the length problems associated with hip surgery is found in the September, 2001 Journal of Arthroplasty, Volume 16, entitled "Correction of Limb-Length Inequality During Total Hip Arthroplasty".

One method for comparing leg length before and after hip surgery is described within U.S. Pat. No. 6,027,507 entitled "Leg Length Gauge for Total Hip Replacement", wherein a removable gauge having pin-receiving apertures is employed.

U.S. Pat. No. 5,606,590 entitled "Surgical Laser Beam-based Alignment System and Method" describes a sophisticated x-ray console that includes a laser source and lens for providing alignment during orthopedic surgery.

A further use of a laser distance detector for manufacturing operations is found in U.S. Pat. No. 4,733,969 entitled "Laser Probe for Determining Distance."

This arrangement employs lenses along with an electronic circuit, which functions as a coordinate measuring machine.

U.S. patent application Ser. No. 09/679,622 now U.S. Pat. No. 6,383,149 entitled "Laser Length Discrepancy Device" describes a pair of laser diodes separated a fixed distance from each other within a hand-held console for determining the position of hip and leg after hip replacement surgery for allowing adjustment thereto. However, upon the occurrence of heavy bleeding or bruise formation, some additional time is required to clean up the leg portion for providing visual access to the reflection of the laser beam from the hip.

It would be economically advantageous to utilize the precision focus of an inexpensive laser diode in combination with an extended pin, after hip surgery without having to thoroughly clean the surface of the hip to determine the position thereof.

One purpose of the instant invention is to provide a simple, non-invasive arrangement of an extended pin and a laser diode for determining pre-operative and post-operative limb and joint distance for maintaining or correcting the distance after surgical joint replacement.

SUMMARY OF THE INVENTION

A hand-held measurement console in the form of an enclosure containing an extended pin and a laser diode is used in conjunction with a pair of temporary markers in the form of screws, indelible markings and the like, to determine a reference distance prior to joint replacement surgery. Immediately after surgery, the lasers are directed on the temporary markers to compare the post surgery distance to the reference distance and appropriate adjustments are made to cause the post-surgery distance to correspond to the pre-surgery reference distance or the desired leg length correction.

DESCRIPTION OF THE PREFERRED EMBODIMENT

Figure 1:
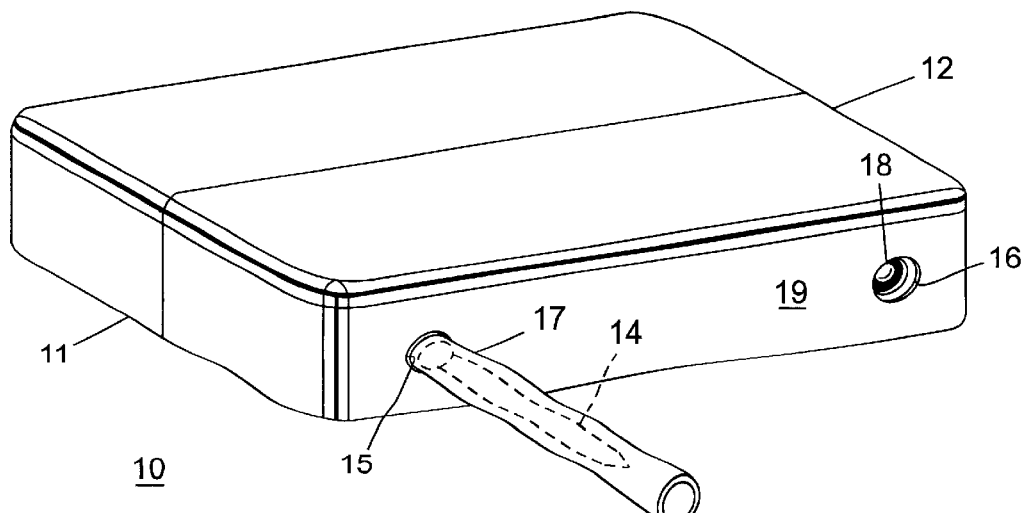
FIG. 1 is an enlarged top front perspective view of the length comparison device according to the invention.

The length comparison device 10, according to the invention, is shown in FIG. 1 to consist of a plastic case 11 to which a plastic cover 12 is removably attached. A first opening 15 is formed within the front 19 of the case 11 for providing transmission from a proximate laser diode 17 and a second opening 16 is formed therein for providing transmission from a distal laser diode 18. The proximate and distal lasers 17, 18 are class 3A low voltage 635 nanometer diodes turned on and off by means of the low voltage switch 14 in the manner to be described below.

Figure 2:
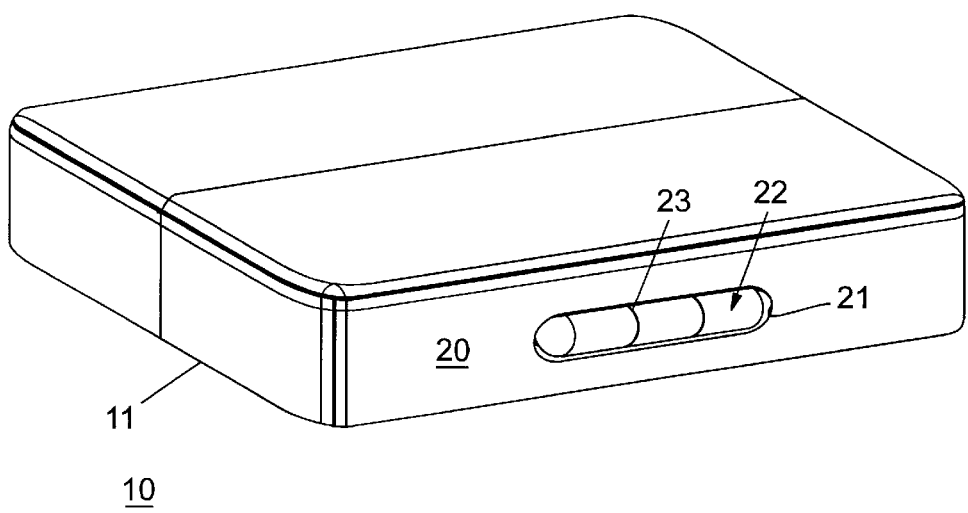
FIG. 2 is an enlarged top rear perspective view of the length comparison device of FIG. 1.

The rear 20 of the length comparison device 10 is shown in FIG. 2 to depict the level gauge 22 extending within the elongated aperture 21 formed within the rear 20 of the case 11. The level gauge is of the type that includes a pair of level lines 23 and a bubble (not shown) for insuring precision line-up of the proximate and distal laser diodes 17, 18 in the manner to be described below.

Figure 3:
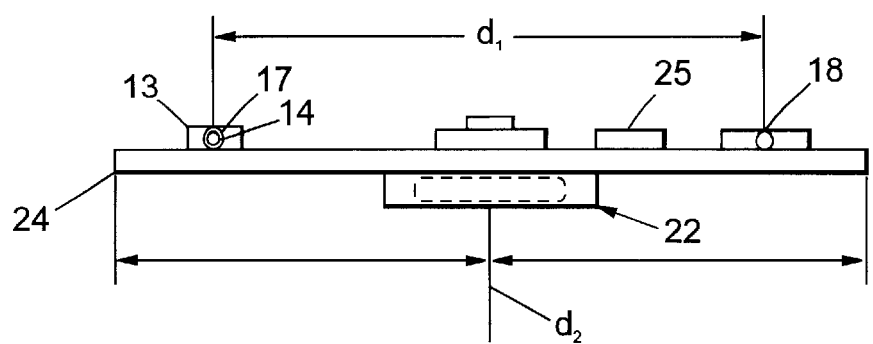
FIG. 3 is front view of the circuit board and components contained within the length comparison device of FIGS. 1 and 2.
Figure 4:
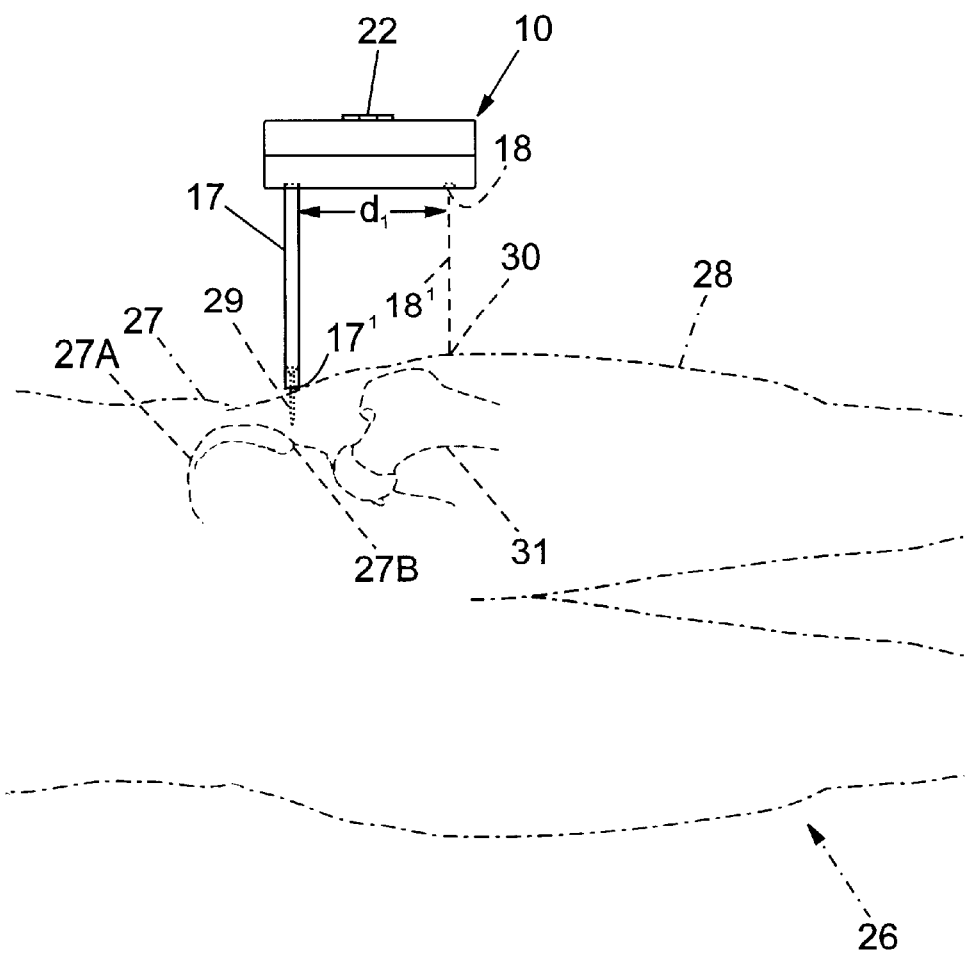
FIG. 4 is top perspective view of the length comparison device of FIGS. 1 and 2 relative to a person, as shown in phantom.

The arrangement of the proximate and distal lasers 17, 18 within the length comparison device 10 of FIG. 1 is best seen by now referring to the printed circuit board 24 shown in FIG. 3. The proximate and distal lasers 17, 18 are arranged a predetermined distance $d_1$ on the top of the printed circuit board 24 on opposite sides of the push button switch 14 and 1.5 volt dry cell miniature batteries as indicated at 25. The level gauge 22 is positioned on the bottom of the printed circuit board 24 at the center thereof as indicated at $d_2$. One use of the length comparison device 10 for determining the positioning of a hip 27 relative to a leg 28 of a patient 26 before and after hip replacement surgery is depicted 30 in FIG. 4.

During the hip replacement surgery, the acetabulum 27A is exposed and a short self-tapping surgical-type screw 29 is inserted into the pelvis as indicated at 27B. It is noted that the screw 29 is out of the way during the hip replacement procedure and serves as a reproducible, non-moving target during the procedure. Before dislocating the hip 27, the patient's leg 28 is held in a level position and the length comparison device 10 is employed in the following manner. The length comparison device 10 is arranged proximate the hip 27 and leg 28, and the level gauge 22 is viewed for adjusting the length comparison device to a level position relative to the patient's leg and hip. The proximate laser 17 is focused on the screw 29 as indicated at 17' and a drill hole 30 is formed at the point of focus of the distal laser 18 at the predetermined distance $d_1$ on the patient's leg 28 over the greater trochanter 31, as indicated at 18'. Although a drill hole 30 is indicated, a colored dye could be used alternatively. Upon replacement of the hip 27, the procedure is repeated for comparing the positional relationship between the proximate and distal lasers 17, 18 via the screw 29, screw hole 30, and focus beams 17', 18'. The leg 28 is then shortened or lengthened to compensate for any change in the predetermined distance $d_1$.

Although the simple length comparison unit 10 is depicted for hip replacement surgery, it is understood that the same unit can be used with other types corrective and replacement surgery to correct for post-operative distance changes.

What is claimed is:

1. A hand-held surgical position indicator comprising:
   a cover and a case joined together to form an enclosure;
   a locating pin extending from said case for determining a first position on a patient's hip before and after surgery;
   a light source on said case arranged a fixed distance from said pin for projecting a light beam on said patient's leg to determine a first position on said patient's leg before surgery and a second position on said patient's leg after surgery;
   whereby said first and said second positions on said patients leg are compared to determine any difference thereof.

2. The position indicator of claim 1 wherein said fixed distance comprises between 3 and 6 inches.

3. The position indicator of claim 1 further including a level gauge on said case providing vertical alignment between said locating pin and said light beam.

4. A method for determining a fixed reference distance prior and subsequent to joint replacement surgery comprising the steps of:
   providing a locating pin extending from a case for determining a first position on a patient's hip before and after surgery;
   arranging a light source on said case a fixed distance from said pin for projecting a light beam on said patient's leg to determine a first position on said patient's leg before surgery and a second position on said patient's leg after surgery; and
   comparing said first and said second positions on said patients leg to determine any difference thereof.

5. The method of claim 4 including the steps of:
   providing a level gauge on said case; and
   aligning said extending pin and said laser diode with said hip and leg.

* * * * *